United States Patent [19]

Cozzi et al.

[11] Patent Number: 5,246,956
[45] Date of Patent: Sep. 21, 1993

[54] N-IMIDAZOLYL DERIVATIVES OF SUBSTITUTED ALKOXYIMINO TETRAHYDRONAPHTHALENES AND CHROMANS HAVING ANTITHROMBOXANE $A_2$ ACTIVITY

[75] Inventors: Paolo Cozzi, Milan; Antonio Giordani, Pavia; Arsenia Rossi, Dalmine; Patricia Salvati, Arese; Corrado Ferti, Barlassina, all of Italy

[73] Assignee: Farmitalia Carlo Erba S.r.l., Milan, Italy

[21] Appl. No.: 830,876

[22] Filed: Feb. 4, 1992

[30] Foreign Application Priority Data

Feb. 11, 1991 [GB] United Kingdom ............... 9102862

[51] Int. Cl.$^5$ ............... A61K 31/415; A61K 31/44; C07D 409/44; C07D 409/08
[52] U.S. Cl. ............................ 514/397; 514/63; 514/337; 514/341; 514/399; 548/110; 548/311.4; 548/315.1; 548/336.1; 546/269; 546/278
[58] Field of Search ............... 548/110, 336, 335, 346, 548/311.4, 336.1; 514/397, 399, 341, 63; 546/278, 269

[56] References Cited

U.S. PATENT DOCUMENTS 4,710,502  12/1987  Wright, Jr. et al. .
5,006,153   4/1991  Lai et al. .

FOREIGN PATENT DOCUMENTS 0135177   3/1985  European Pat. Off. .
WO90/03970 4/1990  PCT Int'l Appl. .
2071655    9/1981  United Kingdom .

OTHER PUBLICATIONS

Derwent Publications Ltd., 86-171236/27 & FR 2573-430-A, Oct. 31, 1984.
Derwent Publications Ltd., 88-243443/35 & EP 275-131-A, Jan. 14, 1987.
Derwent Publications Ltd., 85-001143/01 & DE 3420-592-A, Jun. 20, 1983.
Derwent Publications Ltd., 12191 K/06 & BE 893-917, Jul. 23, 1981.
Derwent Publications Ltd., 84-017853/04 & BE 897-207-A, Jul. 5, 1982.

Primary Examiner—Patricia L. Morris
Attorney, Agent, or Firm—Oblon, Spivak, McClelland, Maier & Neustadt

[57] ABSTRACT

The invention provides new imidazole containing alkoxyimino derivatives of tetrahydronaphthalene and chroman of general formula (I)

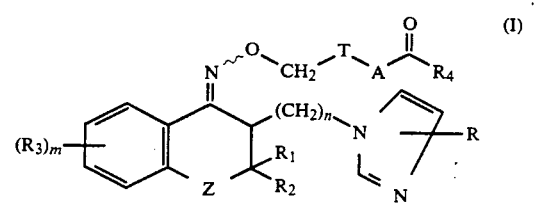

wherein
Z is —$CH_2$—or—O—;
m is an integer of 1 to 4;
n is zero of 1;
T is a straight or branched saturated $C_1$-$C_6$ hydrocarbon chain or $C_2$-$C_5$ alkenylene chain;
A is a bond or a divalent group consisting of —Si(R'R")—; —O—$CH_2$—,—$CF_2$—,C(R'R")—,vinylene or isopropenylene, wherein each of R' and R" being the same or different is hydrogen or $C_1$-$C_4$ alkyl;
R is hydrogen or $C_1$-$C_4$ alkyl;
$R_1$ and $R_2$, being the same, are hydrogen or methyl, or one of $R_1$ and $R_2$ is hydrogen and the other is
a) a $C_1$-$C_8$ alkyl group;
b) a $C_5$-$C_8$ cycloalkyl or $C_5$-$C_8$ cycloalkyl-$C_1C_4$ alkyl group, wherein the cycloalkyl group or moiety is unsubstituted or substituted by 1 to 4 $C_1$-$C_4$ alkyl groups; or
c) an aryl or aryl-$C_1$-$C_4$ alkyl group, wherein the aryl group or the aryl moiety is unsubstituted or substituted by 1 to 4 substituents independently chosen from halogen, hydroxy, $C_1$-$C_4$ alkyl, trihalo-$C_1$-$C_4$
(Abstract continued on next page.)

alkyl, $C_1$-$C_4$ alkoxy, $C_1$-$C_4$ alkylthio and $C_1$-$C_4$ alkylsulfonyl;

$R_3$ is hydrogen or a substituent chosen from halogen, hydroxy, $C_1$-$C_4$ alkyl, trihalo-$C_1$-$C_4$ alkyl, $C_1$-$C_4$ alkoxy, $C_1$-$C_4$ alkylthio and $C_1$-$C_4$ alkylsulfonyl;

$R_4$ is an —$OR_5$ or —$N(R_5 R_6)$ group, wherein each of $R_5$ and $R_6$ independently is hydrogen, $C_1$-$C_6$ alkyl, phenyl or benzyl;

and the pharmaceutically acceptable salts thereof, which are useful in the treatment of a disease state in which an enhancement of $TxA_2$ synthesis exerts a pathogenic effect.

6 Claims, No Drawings

N-IMIDAZOLYL DERIVATIVES OF SUBSTITUTED ALKOXYIMINO TETRAHYDRONAPHTHALENES AND CHROMANS HAVING ANTITHROMBOXANE $A_2$ ACTIVITY

The present invention relates to new imidazole containing alkoxy-imino derivatives of tetrahydronaphthalene and chroman, to a process for their preparation, to pharmaceutical compositions containing them and to their use as therapeutic agents.

The present invention provides novel compounds having the following general formula(I)

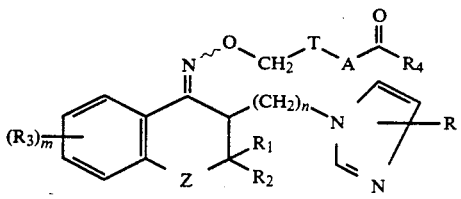

wherein
Z is —CH$_2$—or—O—;
m is an integer of 1 to 4;
n is zero or 1;
T is a straight or branched, saturated or unsaturated C$_1$-C$_6$ hydrocarbon chain, or a phenylene radical;
A is a bond or a divalent group consisting of —Si(R'R")—; —O—CH$_2$—, —CF$_2$—,C(R',R'-')—,vinylene or isopropenylene, wherein each of R' and R" being the same or different is hydrogen or C$_1$-C$_4$ alkyl;
R is hydrogen or C$_1$-C$_4$ alkyl;
R$_1$ and R$_2$, being the same, are hydrogen or methyl, or one of R$_1$ and R$_2$ is hydrogen and the other is
a) a C$_1$-C$_8$ alkyl group;
b) a C$_5$-C$_8$ cycloalkyl or C$_5$-C$_8$ cycloalkyl-C$_1$-C$_4$ alkyl group, wherein the cycloalkyl group or moiety is unsubstituted or substituted by 1 to 4 C$_1$-C$_4$ alkyl groups; or
c) an aryl or aryl-C$_1$-C$_4$ alkyl group, wherein the aryl group or the aryl moiety is unsubstituted or substituted by 1 to 4 substituents independently chosen from halogen, hydroxy, C$_1$-C$_4$ alkyl, trihalo-C$_1$-C$_4$ alkyl, C$_1$-C$_4$ alkoxy, C$_1$-C$_4$ akylthio and C$_1$-C$_4$ alkylsulfonyl;
R$_3$ is hydrogen or a substituent chosen from halogen, hydroxy, C$_1$-C$_4$ alkyl, trihalo-C$_1$-C$_4$ alkyl, C$_1$-C$_4$ alkoxy, C$_1$-C$_4$ alkylthio and C$_1$-C$_4$ alkylsulfonyl;
R$_4$ is an —OR$_5$ or —N(R$_5$ R$_6$)group, wherein each of R$_5$ and R$_6$ independently is hydrogen, C$_1$-C$_6$ alkyl, phenyl or benzyl;
and the pharmaceutically acceptable salts thereof.

The invention also includes within its scope all the possible isomers, stereoisomers and their mixtures and the metabolites and the metabolic precursor or bioprecursor of the compounds of formula (I).

In particular the compounds of formula (I) exhibit either E or Z isomerism about the oximic double bond. Both the single E and Z isomers of the compounds of formula (I) and their mixtures are also included within the scope of the present invention.

When R$_1$ or R$_2$ is a C$_1$-C$_8$ alkyl group, it may be a branched or straight chain alkyl group, for instance octyl, heptyl, hexyl, pentyl, butyl, t. butyl, propyl, ethyl and methyl. When R$_1$ or R$_2$ is a cycloalkyl or cycloalkyl-alkyl group as defined above under b), the cycloalkyl group or the cycloalkyl moiety is preferably a cyclopentyl, cyclohexyl or cycloheptyl group, in particular cyclohexyl.

Accordingly, when R$_1$ or R$_2$ is a C$_5$-C$_8$ cycloalkyl-C$_1$-C$_4$ alkyl group, it is e.g. a cyclopentyl-, cyclohexyl- or cycloheptyl-C$_1$-C$_2$ alkyl group, in particular cyclohexylmethyl or cyclohexylethyl.

When the cycloalkyl group or the cycloalkyl moiety is substituted by more than one alkyl group, each alkyl group may be the same or different. When substituted the cycloalkyl group or moiety is preferably substituted by one or two C$_1$-C$_4$ alkyl groups.

When R$_1$ or R$_2$ is an aryl or arylalkyl group as defined above under c), the aryl group or the aryl moiety may be an aromatic or heteroaromatic group, for example phenyl, pyridyl, thienyl and naphtyl in particular phenyl, thienyl and pyridyl.

According to the definition of R$_1$, R$_2$ as an aryl or arylalkyl group given hereabove, a pyridyl group is preferably a 2- or 3-pyridyl group; a thienyl group is preferably a 2- or 3-thienyl group and a naphthyl group is preferably a 1- or 2-naphthyl group.

Accordingly, when R$_1$ or R$_2$ is an aryl —C$_1$-C$_4$ alkyl group it is e.g. a phenyl-, pyridyl- or thienyl-C$_1$-C$_2$ alkyl group, in particular a benzyl, pyridylmethyl or thienylmethyl group. When an aryl group or an aryl moiety is substituted as defined above under c), it is preferably substituted by one two or three, in particular one or two, substituents as defined above.

When T is a hydrocarbon chain it is preferably an alkylene or alkenylene radical, for example C$_1$-C$_5$ alkylene chain, particular —C$_2$—,—C$_2$—CH$_2$—, or —CH$_2$—CH$_2$—CH$_2$— or —CH$_2$—CH$_2$—CH$_2$—CH$_2$— or a C$_2$-C$_5$ alkenylene chain, in particular —CH=CH—, —CH$_2$—CH=CH— or —CH=CH—CH$_2$—.

When T is a phenylene radical, it is e.g. a 1,2,-,1,3- or 1-4-phenylene, in particular a 1,3-phenylene radical.

When m, being as defined above, is higher than 1, then each R$_3$ substituent may be independently the same or different. When R$_5$ and/or R$_6$ is a C$_1$-C$_6$ alkyl group it is, e.g., methyl, ethyl, propyl, isopropyl, butyl or tert-butyl, more preferably methyl or ethyl.

The alkyl, alkoxy and alkylthio groups may be branched or straight chain groups.

A C$_1$-C$_4$ alkyl group is e.g. methyl, ethyl, propyl, isopropyl, butyl or tertbutyl, more preferably methyl or butyl.

A C$_1$-C$_4$ alkoxy group is e.g. methoxy, ethoxy, propoxy, isopropoxy, butoxy or tert-butoxy, preferably methoxy, ethoxy or propoxy.

A C$_1$-C$_4$ alkylthio group is e.g. methylthio, ethylthio, propylthio or butylthio, in particular methylthio or ethylthio.

A C$_1$-C$_4$ alkylsulfonyl group is e.g. ethylsulfonyl and methylsulfonyl, in particular methylsulfonyl.

A trihalo-C$_1$-C$_4$ alkyl group is e.g. a trihaloethyl or trihalomethyl group, in particular trihalomethyl. A trihalomethyl group is e.g. trichloromethyl or trifluoromethyl, in particular trifluoromethyl.

A halogen atom is suitably bromine, chlorine or fluorine, preferably it is bromine or fluorine. Pharmaceutically acceptable salts of the compounds of the invention include acid addition salts, with inorganic, e.g. nitric, hydrochloric, hydrobromic, sulphuric, perchloric and phosphoric acids, an organic, e.g. acetic, propionic, glycolic, lactic, oxalic, malonic, malic, maleic, tartaric, citric, benzoic, cinnamic, mandelic and salycylic acids, and salts with inorganic, e.g. alkali metal, especially sodium or potassium, bases or alkaline-earth metal, especially calcium or magnesium, bases, or with organic bases, e.g. alkylamines, preferably triethylamine.

As stated above the present invention also includes within its scope pharmaceutically acceptable bioprecursor (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein,

Z is —$CH_2$— or —O—;
m is 1 or 2;
n is zero;
T is a $C_1$-$C_5$ alkylene or $C_2$-$C_5$ alkenylene chain;
A is a bond or a divalent group chosen from —O—$CH_2$—,—$CF_2$—,—C(R'R'')— and Si(R'R''')—, wherein each of R' and R'', being the same or different is hydrogen or methyl;
R is hydrogen;
$R_1$ and $R_2$ are both hydrogen, or one of $R_1$ and $R_2$ is hydrogen and the other is:
a') $C_1$-$C_4$ alkyl;
b') $C_5$-$C_7$ cycloalkyl or $C_5$-$C_7$ cycloalkyl-methyl group;
c') a phenyl or benzyl group, wherein the phenyl ring or the phenyl moiety is unsubstituted or substituted by one, two or three substituents independently chosen from halogen, hydroxy, $C_1$-$C_4$ alkyl, trihalo-$C_1$-$C_4$ alkyl, $C_1$-$C_4$ alkoxy, alkylthio and $C_1$-$C_4$ alkylsulfonyl; or
d) a thienyl, thienylmethyl, pyridyl or pyridylmethyl group, wherein the heterocyclic ring or moiety is unsubstituted or substituted by one or two substituents chosen from halogen, trifluoromethyl, hydroxy, $C_1$-$C_4$ alkyl and $C_1$-$C_4$ alkoxy;
$R_3$ is hydrogen, halogen, trifluoromethyl, $C_1$-$C_4$ alkylsulfonyl or $C_1$-$C_4$ alkoxy;
$R_4$ is an —$OR_5$ or —$NHR_5$ group, wherein $R_5$ is hydrogen or $C_1$-$C_4$ alkyl; and the pharmaceutically acceptable salts thereof.

Examples of preferred compounds according to the present invention are the following compounds, either as Z or E isomers or Z,E-mixtures of said isomers:

1) 5-[[2,3-dihydro-3-(1H-imidazol-1-yl)-4H-1-benzopyranylindene]aminoxy]pentanoic acid;
2) 5-[[2-methyl-3-(1H-imidazol-1-yl)-2,3-dihydro-4H-1-benzopyranylidene]aminoxy]pentanoic acid;
3) Ethyl-5-[[2-methyl-3-(1H-imidazol-1-yl)-2,3-dihydro-4H-1-benzopyranylidene]aminoxy]pentanoate;
4) 6-[[2-methyl-3-(1H-imidazol-1-yl)-2,3-dihydro-4H-1-benzopyranylidene]-aminoxy]hexanoic acid;
5) 6-[[2-phenyl-3-(1H-imidazol-1-yl)-2,3-dihydro-4H-1-benzopyranylidene]aminoxy]hexanoic acid;
6) Ethyl-6-[[2-phenyl-3-(1H-imidazol-1-yl)-2,3-dihydro-4H-1-benzopyranylidene]aminoxy]hexanoate;
7) 5-[[2-phenyl-3-(1H-imidazol-1-yl)-2,3-dihydro-4H-1-benzopyranylidene]aminoxy]pentanoic acid;
8) Ethyl-5-[[2-phenyl-3-(1H-imidazol-1-yl)-2,3-dihydro-4H-1-benzopyranylidene]aminoxy]pentanoate;
9) 4-[[2-(3,4-dimethoxyphenyl)-3-(1H-imidazol-1-yl)-2,3-dihydro-6-methoxy-4-1-benzopyranylidene]aminoxy]butanoic acid;
10) 5-[[2-phenyl-3-(1H-imidazol-1-yl)-2,3-dihydro-6-methoxy-4H-1-benzopyranylidene]aminoxy]pentanoic acid;
11) 6-[[2-phenyl-3-(1H-imidazol-1-yl)-2,3-dihydro-6-methoxy-4H-1-benzopyranylidene]aminoxy]hexanoic acid;
12) Methyl-6-[[2-phenyl-3-(1H-imidazol-1-yl)-2,3-dihydro-6-methoxy-4H-1-benzopyranylidene]aminoxy]hexanoate;
13) 6-[[2-phenyl-3-(1H-imidazol-1-yl)-2,3-dihydro-6-nbutoxy-4H-1-benzopyranylidene]aminoxy]hexanoic acid;
14) 5-[[2-(3,4-dimethoxyphenyl)-3-(1H-imidazol-1-yl)-2,3-dihydro-6-methoxy-4H-1-benzopyranylidene]aminoxy]-pentanoic acid;
15) 6-[[2-(3,4-dimethoxyphenyl)-3-(1H-imidazol-1-yl)-2,3-dihydro-6-methoxy-4H-1-benzopyranylidene]aminoxy]-hexanoic acid;
16) 5-[[(4-fluorophenyl)-3-(1H-imidazol-1-yl)-2,3-dihydro-6-fluoro-4H-1-benzopyranylidene]aminoxy]pentanoic acid;
6-[[2-phenyl-3-(1H-imidazol-1-yl)-2,3-dihydro-6-fluoro-4H-1-benzopyranylidene]aminoxy]hexanoic acid;
18) 3-[[2-(4-fluorophenyl)-3-(1H-imidazol-1-yl)-2,3-dihydro-6-fluoro-4H-1-benzopyranylidene]aminoxy]propyloxyacetic acid;
19) 3-[[2-(4-fluorophenyl)-3-(1H-imidazol-1-yl)-2,3-dihydro-6-fluoro-4H-1-benzopyranylidene]aminoxy]propyloxyacetamide;
20) 5-[[2-(4-fluorophenyl)-3-(1H-imidazol-1-yl)-2,3-dihydro-6-fluoro-4H-1-benzopyranylidene]aminoxy]pentyloxyacetic acid;
21) 2-[[2-(4-fluorophenyl)-3-(1H-imidazol-1-yl)-2,3-dihydro-6-fluoro-4H-1-benzopyranylidene]aminoxy]ethyloxyacetic acid;
22) 6-[[2-cyclohexyl-3-(1H-imidazol-1-yl)-2,3-dihydro-6-fluoro-4H-1-benzopyranylidene]aminoxy]hexanoic acid;
23) 2-[[2-cyclohexyl-3-(1H-imidazol-1-yl)-2,3-dihydro-6-fluoro-4H-1-benzopyranylidene]aminoxy]propyloxyacetic acid;
24) 5-[[2-(thien-2-yl)-3-(1H-imidazol-1-yl)-2,3-dihydro-4H-1-benzopyranylidene]aminoxy]pentanoic acid;
25) 6-[[2-(thien-2-yl)-3-(1H-imidazol-1-yl)-2,3-dihydro-4H-1-benzopyranylidene]aminoxy]hexanoic acid;
26) 5-[[2-(thien-3-(1H-imidazol-1-yl)-2,3-dihydro-4H-1-benzopyranylidene]aminoxy]pentanoic acid;
27) 6-[[2-(thien-3-yl)-3-(1H-imidazol-1-yl)-2,3-dihydro-4H-1-benzopyranylidene]aminoxy]hexanoic acid;
28) 3-[[2-(4-fluorophenyl)-3-(1H-imidazol-1-yl)-2,3-dihydro-6-trifluoromethyl-4H-1-benzopyranylidene]aminoxy]propyloxyacetic acid;
29) 6-[[2-benzyl-3-(1H-imidazol-1-yl)-2,3-dihydro-4H-1-benzopyranylidene]aminoxy]hexanoic acid;
30) 2-[[2-((4-fluorophenyl)methyl)-3-(1H-imidazol-1-yl)-2,3-dihydro-6-fluoro-4H-1-benzopyranylidene]aminoxy]ethyloxyacetic acid;
31) 6-[[2-phenyl-3-((1H-imidazol-1-yl)methyl)-2,3-dihydro-4H-1-benzopyranylidene]aminoxy]hexanoic acid;
32) 5-[[2-(1H-imidazol-1-yl)-1,2,3,4-tetrahydro-1-naphthylidene]aminoxy]pentanoic acid;
33) 5-[[2-(1H-imidazol-1-yl)-7-methoxy-1,2,3,4-tetrahydro-1-naphtylidene]aminoxy]pentanoic acid;
34) Ethyl-5-[[2-(1H-imidazol-1-yl)-1,2,3,4-tetrahydro-1-naphthylidene]aminoxy]pentanoate;
35) 5-[[2-(1H-imidazol-1-yl)-3-methyl-1,2,3,4-tetrahydro-1-naphthylidene]aminoxy]pentanoic acid;

36) 6-[[2-(1H-imidazol-1-yl)-3-methyl-1,2,3,4-tetrahydro-1-naphthylidene]aminoxy]hexanoic acid;
37) 6-[[2-(1H-imidazol-1-yl)-3-phenyl-1,2,3,4-tetrahydro-1-naphthylidene]aminoxy]hexanoic acid;
and the pharmaceutically acceptable salts thereof. The structural formulae of the above-numbered compounds, indicated according to their progressive number, are reported in the following table:

| comp. | Z | m | $R_1$ | $R_2$ | $R_3$ | R | T | A | $R_4$ |
|---|---|---|---|---|---|---|---|---|---|
| 1 | O | 1 | H | H | H | H | $(CH_2)_3$ | bond | OH |
| 2 | O | 1 | H | $CH_3$ | H | H | $(CH_2)_3$ | " | OH |
| 3 | O | 1 | H | $CH_3$ | H | H | $(CH_2)_3$ | " | OEt |
| 4 | O | 1 | H | $CH_3$ | H | H | $(CH_2)_4$ | " | OH |
| 5 | O | 1 | H | Ph | H | H | $(CH_2)_4$ | " | OH |
| 6 | O | 1 | H | Ph | H | H | $(CH_2)_4$ | " | OEt |
| 7 | O | 1 | H | Ph | H | H | $(CH_2)_3$ | " | OH |
| 8 | O | 1 | H | Ph | H | H | $(CH_2)_3$ | " | OEt |
| 9 | O | 1 | H | (3,4-CMe)Ph | 2-$OCH_{23}$ | H | $(CH_2)_2$ | " | OH |
| 10 | O | 1 | H | Ph | 2-$OCH_3$ | H | $(CH_2)_3$ | " | OH |
| 11 | O | 1 | H | Ph | 2-$OCH_3$ | H | $(CH_2)_4$ | " | OH |
| 12 | O | 1 | H | Ph | 2-$OCH_3$ | H | $(CH_2)_4$ | " | OMe |
| 13 | O | 1 | H | Ph | 2-$OC_4H_9$ | H | $(CH_2)_4$ | bond | OH |
| 14 | O | 1 | H | (3,4-OMe)Ph | 2-$OCH_3$ | H | $(CH_2)_3$ | " | OH |
| 15 | O | 1 | H | (3,4-OMe)Ph | 2-$OCH_3$ | H | $(CH_2)_4$ | " | OH |
| 16 | O | 1 | H | (4-F)Ph | 2-F | H | $(CH_2)_4$ | " | OH |
| 17 | O | 1 | H | Ph | 2-F | H | $(CH_2)_4$ | " | OH |
| 18 | O | 1 | H | (4-F)Ph | 2-F | H | $(CH_2)_2$ | $OCH_2$ | OH |
| 19 | O | 1 | H | (4-F)Ph | 2-F | H | $(CH_2)_2$ | $OCH_2$ | $NH_2$ |
| 20 | O | 1 | H | (4-F)Ph | 2-F | H | $(CH_2)_4$ | $OCH_2$ | OH |
| 21 | O | 1 | H | (4-F)Ph | 2-F | H | $(CH_2)$ | $OCH_2$ | OH |
| 22 | O | 1 | H | $C_6H_{11}$ | 2-F | H | $(CH_2)_4$ | bond | OH |
| 23 | O | 1 | H | $C_6H_{11}$ | 2-F | H | $(CH_2)_2$ | $OCH_2$ | OH |
| 24 | O | 1 | H | 2-Thienyl | H | H | $(CH_2)_3$ | bond | OH |
| 25 | O | 1 | H | 2-Thienyl | H | H | $(CH_2)_4$ | bond | OH |
| 26 | O | 1 | H | 3-Thienyl | H | H | $(CH_2)_3$ | " | OH |
| 27 | O | 1 | H | 3-Thienyl | H | H | $(CH_2)_4$ | " | OH |
| 28 | O | 1 | H | (4-F)Ph | 2-$CF_3$ | H | $(CH_2)_2$ | $OCH_2$ | OH |
| 29 | O | 1 | H | $PhCH_2$ | H | H | $(CH_2)_4$ | bond | OH |
| 30 | O | 1 | H | (4-F)$PhCH_2$ | 2-F | H | $(CH_2)$ | $OCH_2$ | OH |
| 31 | O | 1 | H | Ph | H | H | $(CH_2)_4$ | bond | OH |
| 32 | $CH_2$ | 1 | H | H | H | H | $(CH_2)_3$ | " | OH |
| 33 | $CH_2$ | 1 | H | H | 2-OMe | H | $(CH_2)_3$ | " | OH |
| 34 | $CH_2$ | 1 | H | H | H | H | $(CH_2)_3$ | " | OEt |
| 35 | $CH_2$ | 1 | H | $CH_3$ | H | H | $(CH_2)_3$ | " . | OH |
| 36 | $CH_2$ | 1 | H | $CH_3$ | H | H | $(CH_2)_4$ | " | OH |
| 37 | $CH_2$ | 1 | H | Ph | H | H | $(CH_2)_4$ | " | OH |

In the above table: Ph means Phenyl, Me means methyl, Et means Ethyl; n is zero in all the above described compounds, with exception for compound 31 where n is 1.

The compounds of the invention and the salts thereof can be obtained by a process comprising:
a) reacting an oxime of formula (II) or salts thereof

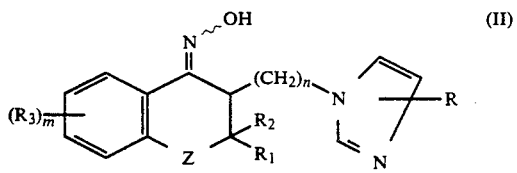

wherein R, $R_1$, $R_2$, R, m, n, and Z are as defined above, with a compound of formula (III)

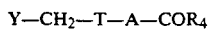     (III)

Y—$CH_2$—T—A—$COR_4$ wherein
T, A and $R_4$ are as defined above and Y is a leaving group;
or b) reacting an oxime of formula (II) as defined above or a salt thereof with a lactone of formula (IV)

wherein
T and A are as defied above, thus obtaining a compound of formula (I) in which $R_4$ is —OH; or
c) reacting a compound of formula (V)

wherein
$R_3$, $R_1$, $R_2$, R, m, n and Z are as defined above, with a compound of formula (VI)

$H_2N$—O—$CH_2$—T—A—$COR_4$     (VI)

wherein
T, A and $R_4$ are as defined above; or
d) reacting a compound of formula (V), as defined above, with a compound of formula (VII)

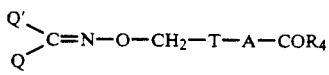

(VII)

wherein

T, A and $R_4$ are as defined above and each of Q and Q' is independently hydrogen, lower alkyl or phenyl; or e) reacting a compound of formula (VIII) or a salt thereof

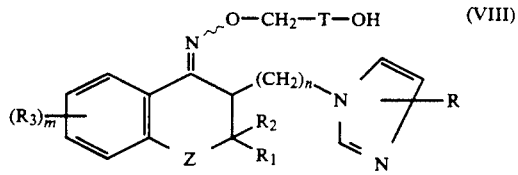

wherein

R, $R_1$, $R_2$, $R_3$, n, m, and T are as defined above, with a compound of formula (IX)

wherein

Y and $R_4$ are as defined above, thus obtaining a compound of formula (I) wherein A is a $-O-CH_2-$ group; and if desired, converting a compound of formula (I) into another compound of formula (I), and/or, if desired converting a compound of formula (I) into a salt thereof, and/or, if desired, converting a salt of a compound of formula (I) into a free compound, and/or, if desired, separating a mixture of isomers of a compound of formula (I) into the single isomers, and/or, if desired, altering by isomerization on the oxime double bond the ratio of E- and Z-isomers of a compound of formula (I) in a mixture thereof so as to obtain a different ratio of such isomers, and/or, if desired, converting by isomerization on the oxime double bond a pure E-isomer of a compound of formula (I) either into a pure Z-isomer thereof or into a mixture of E- and Z-isomers thereof; and/or if desired converting by isomerization on the oxime double bond a pure Z-isomer of a compound of formula (I) either into a pure E-isomer or into a mixture of E- and Z-isomers thereof.

A salt of a compound of formula (II) is for example an alkali metal salt, in particular a sodium or lithium salt.

A salt of a compound of formula (II) may be obtained according to known methods, for example a compound of formula (II) can be reacted with an alkali metal hydride, preferably NaH, in an inert organic solvent, e.g. dimethylformamide.

The leaving group Y in a compound of formula (III) is for example an halo group, in particular a chloro or bromo group, or a residue of an active ester group, in particular mesyl or tosyl.

The reaction of a compound of formula (II), or a salt thereof, with a compound of formula (III) can be carried out according to known methods, for example in the presence of an inert reaction organic solvent e.g. dimethylformamide, dimethylsulfoxide, tert. butanol or benzene, and by addition of an appropriate basic agent e.g. an alkali metal carbonate, in particular sodium carbonate, or sodium hydride or potassium tert. butylate, at a temperature ranging from about 0° C. to reflux temperature.

The reaction of a compound of formula (II) or a salt thereof, as defined above, with a lactone of formula (IV) may be performed according to known methods. For example such reaction can be carried out by following the same reaction conditions described as to the reaction of a compound of formula (II), or a salt thereof, with a compound of formula (III).

The reaction of a carbonyl compound of formula (V) with an aminooxi derivative of formula (VI) can be carried out for example, by dissolving the carbonyl compound in a reaction inert solvent e.g. water, a lower alkanol in particular ethanol, dioxane, tetrahydrofuran, an aromatic hydrocarbon in particular benzene, toluene or xylene, or mixtures of such solvents, and by adding an appropriate basic agent, for example an alkali metal hydroxide in particular sodium or potassium hydroxide, a carbonate or hydrogen carbonate in particular the sodium and potassium ones, or an organic basic agent e.g. a tertiary amine or pyridine.

When one or both of Q and Q' in a compound of formula (VIII) is lower alkyl, it is for example $C_1-C_4$ alkyl in particular methyl or ethyl.

Also the reaction of a compound of formula (V) with a compound of formula (VII) can be carried out according to known methods. For example such reaction can be performed in an inert reaction solvent e.g. acetonitrile or acetic acid, and if required in the presence of a mineral acid e.g. sulphuric or hydrochloric acid, at temperatures ranging from room temperature to reflux temperature.

A salt of a compound of formula (VIII) is for example an alkali metal salt, in particular a sodium or lithium salt.

The leaving group Y in a compound of formula (IX) is for example a halo group, in particular a chloro or bromo group, or a residue of an active ester group, in particular mesyl or tosyl.

The reaction of a compound of formula (VIII), or a salt thereof, with a compound of formula (IX) can be carried out by following the same reaction conditions described above as to the reaction of a compound of formula (II), or a salt thereof, with a compound of formula (III).

The conversion of a compound of formula (I) into another compound of formula (I) can be carried out by methods known in themselves. For example, a compound of formula (I) containing an esterified carboxy group can be converted into the corresponding free carboxylic acid by known methods. In particular a compound of formula (I) in which $R_4$ is an $OR_5$ group wherein $R_5$ being as defined above, is other than hydrogen can be converted by acidic or alkaline hydrolysis into the respective free carboxylic acid. The reaction is preferably carried out at temperatures ranging from about $-5°$ C. to about 50° C.

A compound of formula (I) containing a free carboxy group, such as a compound of formula (I) in which $R_4$ is hydroxy, can be converted into a corresponding esterified carboxy derivative, e.g. a compound of formula (I) in which $R_4$ is an $-OR_5$ group, wherein $R_5$ being as defined above, is other than hydrogen. Such esterification reaction can be carried out according to known methods, preferably via an intermediate reactive derivative of the carboxylic acid, which may be isolated or not, by reaction with the appropriate alcohol of formula $R_5OH_9$ in which $R_5$ being as defined above, is other than hydrogen. The reaction can be carried out in a customary solvent e.g. benzene or toluene, or in the presence of an excess of the alcohol itself of formula R₅OH.

The temperature reaction may range from about 10° C. to about 50° C. Intermediate reactive derivatives of the carboxylic acid may be for example acidic halides, e.g. the chloride, mixed anhydrides e.g. ethoxycarbonyl or tert. butyloxy anhydrides, or a suitable reactive intermediate obtained in situ e.g. by reaction with a diimide e.g., dicyclohexylcarbodiimide, or carbonyl diimidazole.

A compound of formula (I) wherein $R_4$ is hydroxy, i.e. containing a free carboxy group, can be converted into a corresponding compound of formula (I) wherein $R_4$ is a —$NR_5R_6$ group, in which $R_5$ and $R_6$ are as defined above, according to known methods; preferably via an intermediate reactive derivative thereof, which can be isolated or not.

Intermediate reactive derivatives may be active esters e.g. $NO_2$-phenyl esters, or N-hydroxysuccinimide esters, acid halides, preferably chloride, mixed anhydrides e.g. ethoxycarbonyl or tert-butylcarbonyl anhydrides, or the reactive intermediates obtained in situ by reaction of the acid with dicyclohexylcarbodiimide or carbonyl-diimidazole.

For example, a reactive intermediate as defined above, which can be obtained following conventional ways, as those usually employed in the synthesis of peptides, is reacted with ammonia or an appropriate amine in a customary solvent or with an excess of the amine itself at temperatures ranging from about −10° C. to about 50° C.

The optional salification of a compound of formula (I) as well as the conversion of a salt into the free compound and the separation of a mixture of isomers into the single isomers may be carried out by conventional methods.

For example the separation of a mixture of geometric isomers, e.g. Z- and E-isomers, may be carried out by fractional crystllization from a suitable solvent or by chromatography, either column chromatography or high pressure liquid chromatography.

The optional isomerization on the oxime double bond in a compound of formula (I), which is an equilibrium reaction, can be performed according to known methods; preferably in the presence of a mineral acid e.g. hydrochloric acid and/or by heating.

An oxime of formula (II), which in view of the oxime double bond, may exist either as Z or Esomer or as a mixture thereof can be obtained according to known methods. For example a') by reaction of a compound of formula (V), as defined above, with hydroxylamine or an acid addition salt thereof, e.g. hydrochloride or b') by reaction of an oxime of formula (X)

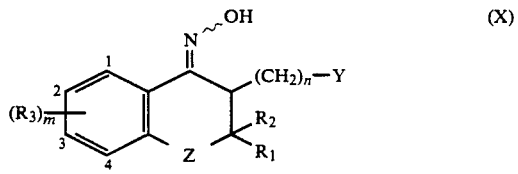

(X)

wherein y, m, n, $R_1$, $R_2$, $R_3$ and Z are as defined above, with imidazole, $C_1$-$C_4$ alkylimidazole or a salt thereof; e.g. following for example the procedure in Arzeim.-Forsch./Drug Res., 29 (II) 1510-13, (1979).

Also an oxime of formula (II), if desired, can be submitted to the same isomerization on the oxime double bond described above as to a compound of formula (I), according to known methods. Similarly, a mixture of Z and E isomers of an oxime of formula (II) can be separated into the single isomers by following customary methods.

The compounds of formula (III), (IV) and (V) are either known compounds or can be obtained by known methods from known compounds. Also the compounds of formula (VI) are either known compounds or can be obtained from known compounds by following known methods, e.g. those described in Tetrahedron (1967), 23, 4441, or in general described in Organic Functional Group Preparation, by S. R. Sandler and W. Karo, Vol. III, chapter X, Academic Press, (1972).

The compounds of formula (VII) can be obtained by reaction of a known compound of formula (XI)

(XI)

wherein Q and Q' are as defined above, with a compound of formula (VI) as defined above, by following the same reaction procedures described above under process c).

Alternatively, a compound of formula (VII) can be obtained from a compound of formula (XI), via the corresponding oxime of formula (XII)

(XII)

wherein Q and Q' are as defined above, by reaction either with a compound either of formula (III) or of formula (IV) by following the same reaction conditions described above under processes a) and b).

The compounds of formula (VIII) can be obtained from known compounds by following procedures similar to those described under processes a), b) c) and d) above.

The compounds of formula IX are known compounds.

The compounds of formula (X) can be obtained, according to a procedure similar to that described under process a') from compounds of formula (XIII)

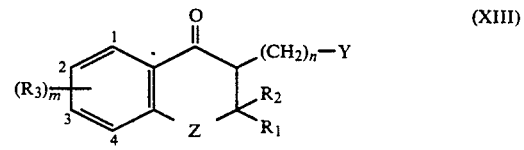

(XIII)

wherein $R_1R_2$, $R_3$, Y, m and n are as defined above,

The compounds of formula (XI) and XIII) are known compounds or can be obtained by following known methods.

When in the intermediate compounds, according to the present invention, groups are present which may interfere with the reactions herein described, these groups can be protected before the reaction takes place and then deprotected at the end of the reaction according to known methods e.g. those used in the chemistry of peptides.

PHARMACOLOGY

Thromboxane (TXA$_2$) is a derivative of arachidonic acid metabolism that aggregates platelets and amplifies their response to a variety of other aggregating agents.

In addition TXA$_2$ contracts vascular, bronchial and tracheal smooth muscle cells and glomerular mesangial cells.

Therefore TXA$_2$ is involved in a variety of pathologies such as: cardiovascular diseases (myocardial infarction and angine), cerebrovascular diseases, (stroke, transient ischemic attack and migrain), peripheral vascular diseases, (nmircroangiopathies), renal diseases (glomerulosclerosis, lupus nephrities, diabetic nephropathy), and respiratory diseases (bronchoncontriction and asthma) and more in general is involved in atherosclerosis.

TXA$_2$ exerts it s action in platelet and smooth muscle cells through the occupancy of receptor(s), the TXA$_2$ receptor(s).

The effects of TXA$_2$ can be counteracted by an agent possessing TXA$_2$ receptors antagonistic properties and/or by an agent inhibiting the enzymes involved in the synthesis of TXA$_2$, in particular TXA$_2$-synthase which catalizes the formation of TXA$_2$ from cyclic endoperpoxides p rostaglandin G$_2$ and prostaglandin H$_2$ without affecting the synthesis of other prostaglandins.

Agents which inhibit TXA$_2$ action either by antagonizing TXA$_2$ and/or inhibiting TXA$_2$-synthase may be expected to be of therapeutic value in the treatment of the above-mentioned diseased and in other pathological conditions in which TXA$_2$ is involved.

The compounds of the present invention, which posses these activities, are believed to be effective in the treatment of a disease state in which an enhancement of TXA$_2$ synthesis exerts a pathogenic effect, for instance those mentioned above.

METHODS

The effects of a representative group of compounds of the invention were evaluated, in comparison with known compounds, on TxB$_2$ synthesis inhibition in vitro, in whole blood of normal rates, and on TxA$_2$ antagonism in a binding assay in washed human platelets.

TxB$_2$ synthesis inhibition

Blood was withdrawn from the abdominal aorta of normal Sprague Dawley rats (Charles River Italy) under light ether anaesthesia. The blood was immediately divided in portions of 0.5 ml and distributed in glass tubes each containing a concentration of the test compound, or of the reference compounds.

Samples were then allowed to clot for 1 hour at 37° C., centrifuged at 3000 rpm for 10 min, and serum collected and stored at $-20°$ C. until assayed. TxB$_2$ levels were determined by RIA according to previously described procedures (Thromb. Res. 17, 3/4, 317, 1980) using a highly sensitive antibody.

Displacement of [$^3$H]—SO 29,548 binding to washed human platelets.

Blood from healthy volunteers of both sexes who had not taken any medication for at least 10 days was collected into one-tenth volume of acid citrate dextrose containing indomethacin (28 $\mu$M). Platelet rich plasma (PRP), obtained by centrifugation of the blood at 200 xg for 20 min. was washed twic (1000 xg for 10 min). The platelets are then resuspended in Tyrode-Hepes buffer (pH 7.4) to a final concentration of $5-10\times10^{-8}$ cells/ml and incubated for 0-60 min at 25° with [$^3$H]—SQ 29,548 (5 nM). For displacement experiments various concentrations ($10^{-9}$–$10^{-4}$M) of competing ligands were added and incubated for 30 min at 25° C. Non-specific binding was determined in the presence of 50 $\mu$M U46619 and was approximately 5% of total binding of [$^3$H]—SQ 29,548. After the incubation, 4 ml of ice-cold TRIS-HCl buffer (10 mM, pH 7.4) was added to each tube and the reaction mixture was immediately filtered by suction through a Whatman GF/C glass filter disc which was washed 2 times with ice-cold TRIS-CH1 (4 ml) and counted for radioactivity by a Packard $\beta$-counter.

The binding data were analysed by computerized non-linear curve fitting using the Ligand program and expressed as ID$_{50}$.

In table 1, as an example the results obtained with the representative compound, according to the present invention, having internal code FCE 27016, in the binding test (washed human platelets) are compared to those obtained with the reference standard compounds, BM 13505 and BM 13177 (Naunyn-Schmideberg's Arch. Pharmacol. 1986, 332 (Sppl.) Abst. 144 S.R. 36; Cardiovasc. Drug Rev. 1988, 6:20-34). These results show that the compound FCE 27016 has an affinity for the receptor greater than those of compounds BM 13505 and BM 13177 and is a patent TxA$_2$ antagonist.

TABLE 1

| Compound | $^3$H SQ 29548 binding displacement (washed human platelet) IC$_{50}$ (M) |
| --- | --- |
| BM 13505 | $1.2 \times 10^{-7}$ |
| BM 13177 | $7.3 \times 10^{-6}$ |
| FCE 27016 | $3.3 \times 10^{-8}$ |

In /table 2, as an example, the results obtained with the representative compound of the invention having internal code FCE 26365, on TxB$_2$ synthesis in normal rats, are compared with those obtained with the reference standard dazoxiben and ASA; limits when calculated are reported in brackets.

The comparative data set out in Table 2 show that FCE 26365 is a potent inhibitor of platelet TxA$_2$ synthase.

TABLE 2

In vitro effect on TxB$_2$ synthesis in normal rats.
Data are expressed as IC$_{50}$ (M) and limits for p = 0.95

| Compound | IC$_{50}$ (M) (whole blood) | LIMITS |
| --- | --- | --- |
| FCE 26365 | $2.7 \times 10^{-8}$ | $(0.95-5.4.10^{-8})$ |
| Dazoxiben | $1.2 \times 10^{-6}$ | $(0.7-1.9 \times 10^{-6})$ |
| ASA | $3.1 \times 10^{-5}$ | $(2.6-3.8 \times 10^{-5})$ |

In the above table 1 and 2 internal code FCE 26365 means (+ —)-(Z)-5 [2-methyl-3-(1H-imidazol-1yl)-2,3-dihydro-4H-1-benzopyranylidene] aminoeypentanoic acid; FCE 27016 means (+ —)-(Z)-6[2-phenyl-3-(1H-imidazol-1-yl)-2,3-dihydro-4H-1-benzopyranylidene]aminoxyhexanoic acid; and ASA means acetylsalicilic acid.

In Table 3, as a further example, the results obtained with the representative compound of the invention (+ —)-(Z)-5-[[2-(3,4-dimethoxyphenyl)-3-(1H-imidazol-1-yl)-2,3-dihydro-6-methoxy-4H-1-benzopyranylidene]aminoxy]-pentanoic acid; (internal code FCE 26603) in inhibition of TxB$_2$ synthesis in rat whole blood and binding displacement of $^3$H SQ 29548 in washed human platelets are compared to those obtained with the reference standard compounds Dazoxiben, BM 13177 and BM 13505.

TABLE 3

| Compound | TxB$_2$ synthesis IC$_{50}$ (M) | $^3$H-SQ 29548 binding displacement IC$_{50}$ (M) |
|---|---|---|
| FCE 26603 | $2.0 \times 10^{-7}$ | $1.0 \times 10^{-7}$ |
| Dazoxiben | $1.2 \times 10^{-6}$ | inactive |
| BM 13177 | inactive | $7.3 \times 10^{-6}$ |
| BM 13505 | inactive | $1.2 \times 10^{-7}$ |

As the compounds of the present invention are both TxA$_2$ synthase inhibitors and PGH$_2$/TxA$_2$ antagonists in the platelets, on the basis of the state of the art, as reported e.g. in J. Clin. Invest. 80, 1435 (1987) and in Adv. Prostaglandins, Thromboxanes, Leukotrienes Res. Vol. 17 (1987) p. 49, these compounds are particularly suitable for the treatment of a disease state in which an enhancement of TxA$_2$ synthesis exerts a pathogenic effect, for instance in those mentioned above.

In particular in the treatment of renal failure the compounds of the invention may be used in association with an angiotensin converting enzyme inhibitor (ACEI), both as separated and substantially concomitant administration. The compounds of the invention can also be used to prevent or treat cyclosporin A-induced nephrosis in mammals.

The compounds of the invention can also be used in association with thrombolytic agents (e.g. tPA, Streptokinase, pro-Urokinase) in order to reduce the dose of the latter required in thrombolytic therapy, and to lower the incidence of reocclusion and possibly haemorrage.

A further application of the compounds of the invention is the prevention and/or treatment of restenosis after percutaneous transluminal angioplasty.

The toxicity of the compounds of the invention is negligible, therefore they can be safely used in therapy. Mice and rats which had been deprived of food for nine hours were treated orally with single administrations of increasing doses of compounds of the invention, then housed and normally fed. In view of their high activity the compounds of the invention can be safely used in medicine.

The therapeutic regimen for the different clinical syndromes must be adapted to the type of pathology, taking into account, as usual, also the route of administration, the form in which the compound is administered and the age, weight and conditions of the subject involved. The oral route is employed, in general, for all conditions requiring such compounds. Preference is given to intravenous injection or infusion for the treatment of acute pathological states. For maintenance regimens the oral or parental, e.g. intramuscular, route is p referred.

The dosage level suitable for oral administration to adult humans of the compounds of the invention, e.g. Z-6-[[2-phenyl-3-(1H-imidazol-1-yl)-2,3-dihydro-4H-benzopyranylidene]aminoxy]hexanoic aicd; may range from about 50 mg to about 500 mg per dose 1 to 3 times a day. Of course, these dosage regimens may be adjusted to provide the optimal therapeutic response.

The nature of the pharmaceutical compositions containing the compounds of this invention in association with pharmaceutically acceptable carriers or diluents will of course, dependent upon the desired route of administration.

The compositions may be formulated in the conventional manner with the usual ingredients. For example, the compounds of the invention may be administered in the form of aqueous or oily solutions, or suspensions, tablets, pills, gelatin capsules, syrups, drops or suppositories.

Thus, for oral administration, the pharmaceutical composition containing the compounds of this invention are preferably tablets, pills or gelatin capsules which contain the active substance together with diluents, such as lactose, dextrose, sucrose, mannitorl, sorbitol, cellulose; lubricants, for instance silica, talc, stearic acid, magnesium or calcium stearate, and/or polyethylene glycos; or they may also contain binders, such as starches, gelatin, methylcellusose, carboxymethylcellulose, gum-arabic, tragacanth, polyvinylpyrololidone; disaggregating agents, such as lecithin, polysorbates, laruylsulphates; and in general, non-toxic and pharmacologicalyy inactive substances used in pharmaceutical formulations. Said pharmaceuticla preparations may be manufactured in known manner, for example by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspesnions or solutions for intramuscular injections may contain together with the active compound a pharmaceutically acceptable carrier, e.g. sterile water, olvie oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following Examples illustrate, but do not limit any way the present invention.

EXAMPLE I (+ −)-(Z)-Ethyl-5-[[2-methyl-3-(1H-imidazol-1-yl)-2,3-dihydro-4H-1-benzopyranylidene]aminoxy]pentanoate (Compound 3).

(+ −)-(Z)-2-Methyl-3-(1H-imidazol-1-yl)-2,3-dihydro-4H-1-benzopyran-4-one oxime (1.7 g, 0.07 moles) is dissolved in dry DMF (30 ml), under dry nitrogen atmosphere and to the resulting solution sodium hydride 80% (0.250 g., 0.015 moles) is added portionwise, under stirring at room temperature. The resulting slurry is stirred further 3 hrs at room temperature, and ethyl 5-bromo pentanoate (1.33 ml; 8.4 mmoles) added dropwise.

The reaction mixture is stirred further 3 hrs., at room temperature, the solvent is evaporated and the residue carefully taken up with ice-cooled water (20 ml).

The resulting mixture is extracted with ethyl acetate (3×30 ml) and the collected organic phases are washed with brine, dried over Na$_2$SO$_4$, and evaporated in vacuo.

The resulting oily material is chromatographed over silica gel using as eluant AcOEt/Hexane/Triethylamine (30:20:7). The pure title compound is obtained as slight yellow oil (g. 1.15).

Microanalysis:
Found: C 64,40; H 7,53; N, 8.27;
Calculated for C$_{20}$H$_{25}$N$_3$O$_4$C64,91; H7,46; N8,41.
$^1$-H-NMR (200 MHz), (CDCl$_3$): ppm:
1,23 (6H, m, —OCHCH$_3$+—COOCH$_2$CH$_3$),
1,5–1,8 (4H, m, —OCH$_2$CH$_2$CH$_2$)
2.27 (2H, m, CH$_2$ COO),
4.0–4.2 (4H, m, —COOCH$_2$+—OCH$_2$CH$_2$),
4,34 (1H, dq, H$_2$),
5,49 (1H, d, H$_3$)
6,8–7,5 (6H, m, H$_6$+H$_7$+H$_e$+imidazole ringe),
7,89 (1H, dd, H$_5$).

As an example, the intermediate oxime used as starting material can be prepared as follows:

(+−)-2-methyl-3-(1H-imidazol-1-yl)-2,3-dihydro-4H-1-benzopyran-4-ne [J.Het.Chem. 21, 311, (1984)], (g. 3.78,m 0.016 moles) is dissolved in 95% ethanol (160 ml), to the resulting solution anhydrous Na$_2$CO$_3$ (3.39 g; 0.032 moles) and hydroxylamine hydrochloride (2.22 g.; 0.032 moles), are added and the resulting reaction mixture is refluxed for 24 hrs..

The solvent is evaporated, and the resulting oily material is dissolved in CHCl$_3$ (150 ml). The organic layer, is washed with water (3×150 ml), dried over CaCl$_2$, and evaporated in vacuo to give a crude material which is chromatographed over silica gel.

elution with CH$_2$Cl$_2$/MeOH/AcOH (90:10:0.4), gives the pure product as a white solid (g. 3.24), melting at 226°–228° C.

$^1$H-NMR (200 MHz, Me$_2$-SO-d$_6$) ppm:
1,08 (3H,d, —O—CH—CH$_3$)
4,43 (1H, dq, H$_2$),
5,80 (1H, d, H$_3$),
6,75–7,60 (6H, m, H$_6$+H$_7$+H$_8$+imidazole ring),
7,84 (1H,dd,H$_5$).

EXAMPLE II (+−)-Z)-[[2-Methyl-3-(1H-imidazol-1-yl)-2,3-dihydro-4H-1-benzopyranylidene]aminoxy]pentanoic acid (Compound 2)

The ester reported in Example I (150 mg., 0.4 mmoles) is dissolved in ethanol (2 ml) and to the resulting solution, NaOH 1N (2 ml, 2 mmoles) is added on stirring at room temperature. The hydrolysis is then completed by stirring the reaction mixture at r.t. an additional hour.

The solvent is evaporated in vacuo, the residue is treated with water (3 ml) and to this ice-cooled mixture, acetic acid is added dropwise until pH.5. The resulting acidic solution is extracted with ethyl acetate, the collected organic extracts are washed with eater, dried over Na$_2$SO$_4$ and evaporated in vacuo.

Residues of acetic acid are removed by coevaporation with toluene and the crude material so obtained is crystalized from ethyl ether, to give compound 2 as colorless solid, (mg.80), melting at 184°–186° C.

Microanalysis:
Found C62,61; H 6,12; N 12,08;
Calculated for C$_{18}$H$_{21}$N$_3$O$_4$ C 62,96;H 6,16; N 12,24.
$^1$H-NMR (200 MHz, CDCl$_3$) ppm:
1,21 (3H,d,—O—CHCH$_3$),
1,5—1,8 (4H, m, —OCH$_2$CH$_2$CH$_2$),
2,29 (2H, m, —CH$_2$—COOH),
4,18 (2H, m, —OCH$_2$CH$_2$,
4,35 (1H,dq, H$_2$),
5,57 (1H,d, H$_3$),
6,70–7,80(6H, m, H$_6$+H$_7$+H$_8$+imidazole ring),
7,91 (1H, dd, H$_5$).

By the same procedure the following compounds can be prepared:

(+−)-(Z)5-[[2,3-dihydro-3-(1H-imidazol-1-yl)-4H-1-benzopyranylidene]aminoxy] pentanoic acid (Compound 1).

mp. 125°–128° C.
Microanalysis:
Found: Cd61,26; H5,83; N12,42;
Calculated for C$_{17}$H$_{19}$N$_3$O$_4$: C 61,99; H 5,81; N 12,76
$^1$H-NMR: (C$_{17}$ H$_{19}$ N$_3$ O$_4$ HCl,200 MHz, CDCl$_3$) ppm:
1,6–1,9 (4H, m, —OCH$_2$CH$_2$CH$_2$—),
2,35 (f2H, m, —CH$_2$COOH),
4,24 (2H, m, —OCH$_2$CH$_2$—),
4,37 (1H, dd, H$_{2a}$),
4,66 (1H, dd, H$_{2b}$),
6,06 (1H, bs, —OCH$_2$CH—C=N—),
7,0–7,4 (5H, m, H$_6$+H$_7$+H$_8$+H$_{4,5}$ of imidazole ring),
7,92 (1H, dd, H$_5$),
8,82 (1H, bs, H$_2$ of imidazole ring).

(+−)—(Z)-6-[[2-methyl-3-(1H-imidazol-1-yl)-2,3-dihydro-4H -1-benzopyranylidene]-aminoxy]hexanoic acid; (Compound 4).

m.p. 133°–135° C.
Microanalysis:
Found: C 63,51; H 6,58; N 11,54;
Calculated for C$_{19}$H$_{23}$N$_3$O$_4$: C 63,85; H 6,49; N 11,76.
$^1$H-NMR (200 MHz, Me$_2$SO-d$_6$)ppm:
1.08 (3H, d, —OCHCH$_3$)
1,05–1,65 (6H, m, —OCH$_2$CH$_2$CH$_2$CH$_2$—)
2,15 (2H, m, —CH$_2$COOH)
4,10 (2H, m, —OCH$_2$CH$_2$—)
4,47 (1H, dq, H$_2$),
5,75 (1H, d, H$_3$),
6,75 (6H, m, H$_6$+H$_7$+H$_8$+imidazole ring),
7,83 (1H, m, H$_5$).

(+−)-(Z)-5-[2-(1H-imidazol-1-yl)-1,2,3,4-tetrahydro-1-naphtylidene]amnoxy]pentanoic acid (Compound 32)

mp. 81°–83° C.
Microanalysis:
Found C 64,04; H 6,87; N 11,01;
Calculated for C$_{18}$H$_{21}$N$_3$O$_3$: C 66,04; H 6,46; N 12,83.
$^1$H-NMR(200 MHz, CDCl$_3$) ppm
1,75 (4H, m, —OCH$_2$CH$_2$CH$_2$—),
2,2 (4H, m, —CH$_2$COOH+H$_3$),
2,7 (2H, m, H$_4$),
4,15 (2H, m, —OCH$_2$CH$_2$CH$_2$—),
5,80 (1H, t, H$_2$),
6,8–7,35 (5H, m, H$_5$+H$_6$+H$_7$+H$_{4,5}$ of imidazole ring),
7,7 (1H, bs, H$_2$ of imidazole ring),
8,01 (1H, dd, H$_8$).

(+−)-(Z)-5-[[2-(1H-imidazol-1-yl)-7-methoxy-1,2,3,4-tetrahydro-1-naphtylidene]aminoxy]pentanoic acid (Compound 33).

m.p. 97°–99° C.
Microanalysis:

Found: C 63,70; H 6,59; N 11,54;
Calculated for $C_{19}H_{23}N_3O_4$: C 63,85; 6,49; N 11,76.
$^1$H-NMR (200 MHz, CDCl$_3$)ppm:
1,4–1,8 (4H,m, —OCH$_2$CH$_2$CH$_2$—),
2,2 (3H, m, —CH$_2$COOH+H$_3$),
2,7 (2H, m, H$_4$),
3,84 (3H, s, —OCH$_3$),
4,15 (2H, m, —OCH$_2$CH$_2$CH$_2$—),
5,79 (1H, t, H$_2$),
6,8–7,1 (4H, m, H$_5$+H$_6$+H$_{4,5}$ of imidazole ring),
7,54 (1H, d,H$_8$),
7,66 (1H, bs, H$_2$ of imidazole ring).
And analogously:
6-[[2-cyclohexyl-3-(1H-imidazol-1-yl)-2,3-dihydro-6-fluoro-4H-1-benzopyranylidene]aminoxy]hexanoic acid; (Compound 22)
2-[[2-cyclohexyl-3-(1H-imidazol-1-yl)-2,3-dihydro-6-fluoro-4H-1-benzopyranylidene]aminoxy]propyloxyacetic acid; (Compound 23)
5-[[2-(1H-imidazol-1-yl)-3-methyl-1,2,3,4-tetrahydro-1-naphthylidene]aminoxy]pentanoic acid;(Compound 35)
6-[[2-(1H-imidazol-1-yl)-3-methyl-1,2,3,4-tetrahydro-1-naphthylidene]aminoxy]hexanoic acid;(Compound 36) and
6-[[2-(1H-imidazol-1-yl)-3-phenyl-1,2,3,4-tetrahydro-1-naphthylidene]hexanoic acid;(Compound 37)

EXAMPLE III (+ −)-(E)-Ethyl-5-[[2-(1H-imidazol-1-yl)-1,2,3,4-tetrahydro-1-naphtylidene]aminoxy]pentanoate (Compound 34)

(+ −)-(E)-2-(1H-imidazol-1-yl)-1,2,3,4-tetrahydronaphtalen-1-one oxime (500 mg; 2.2 mmoles) dissolved in dry DMF (27 ml) is added, under dry nitrogen atmosphere, to a pentane-washed sodium hydride suspension (160 mg NaH 55%; 3.6 mmoles), in dry DMF (10 ml). The resulting reaction mixture is stirred at r.t. for 2 hours. Then ethyl-5-bromopentanoate (0.530 ml; 3.3 mmoles) is added at r.t. and the reaction mixture is stirred at r.t. for 3 hrs., the solvent evaporated in vacuo, and the residue carefully taken up with ice-cooled water and extracted with ethyl acetate. The collected organic phases are dried over Na$_2$SO$_4$ and evaporated to give an oily crude material which is chromatographed over silica gel. By eluting with CH$_2$Cl$_2$/MeOH (95:5), the pure title compound is obtained as a slight yellow oil (250 mg). $^1$H-NMR (200MH$_z$, CDCl$_3$) ppm.
1,23 (3H, t, —COOCH$_3$),
1,75 (4H, m,—OCH$_2$CH$_2$CH$_2$—),
2,3–3,0(6H, m, —CH$_2$COO— +H$_3$+H$_4$),
4,0–4,25(4H, m, —COOCH$_2$CH$_3$+—OCH$_2$CH$_2$—),
5,07 (f1H, dd, H$_2$),
6,8–7,5 (6H, m, H$_5$+H$_6$+H$_7$+imidazole ring),
8,53 (1H, m, H$_8$),

EXAMPLE IV (+ −)-(E)-[[2,3-dihydro-3-(1H-imidazol-1-yl)-4H-1-benzopyranylidene]aminoxy]pentanoic acid. (Compound 1)

(E)-3-(1H-imidazol-1-yl)-2,3-dihydro-4H-1-benzopyran-4-one oxime (1.5 g.;6.5 mmoles) is reacted with ethyl-5-bromopentanoate (2 ml, 13.9 mmoles), but using the same procedure described in Example I, to give (+ −)-(E)-ethyl-5-[[2,3-dihydro-3-(1H-imidazol-1-yl)-4H-1-benzopyranylidene]aminoxy]pentanoate, (1.18 g.), as colorless oil.

Hydrolysis of the above reported ester is then carried out following the same procedure reported in Example II, leading the compound 1, as colorless solid, melting at 125°–127° C.
Microanalysis:
Found: C 61,26; H 5,88; N 12,08
Calculated for $C_{17}H_{19}N_3O_4$ : C 61,99; H 5,81; N 12,76.
$^1$H-NMR: (200 MH$_2$, CDCl$_3$) ppm;
1,6–2,0 (4H, m, —OCH$_2$CH$_2$CH$_2$-),
2,4 (2H, m, —CH$_2$COOH),
4,25(2H, m, —OCH$_2$CH$_2$—),
4,52 (1H, dd, H$_{2a}$),
4,84 (1H, dd, H$_{2b}$),
5,07 (1H, t, —OCH$_2$CH—C=N—),
6,8–7,4 (5H, m, H$_6$+H$_7$+H$_8$+H$_{4,5}$ of imidazole ring),
8,15 (1H, bs, H$_2$ of imidazole ring),
8,55 (1H, dd, H$_5$).
As an example the intermediate oxime used as starting material can be prepared as follows:
3-bromo-2,3-dihydro-4H-1-benzopyran-4-one (37.6 g.,0.17 moles), is suspended in methanol, hydroxylamine hydrochloride (35.5 g., 0.51 moles) is added at room temperature on stirring and the reaction mixture is refluxed for 6 hrs. From the resulting solution a white precipitate is formed by stnding at room temperature overnight. The solid so obtained is filtered and washed with ethy ether to give 30.1 g. of 3-bromo-2,3-dihydro-4H-1-benzopyran-4-one oxime. This compound (29.5 g.; 0.122 moles), is dissolved in CHCl$_3$ (150 ml) and the solution added dropwise to an ice cooled solution of imidazole (25 g.;0.37 moles) in CHCl$_3$ (200 ml), under vigorous stirring.

The resulting solution is stirred at 0° C. for an hour, after this time, water is added, and a white solid is soon formed on stirring.

This is then collected, washed with ethyl ether, and dried to give the desired oxime (15 g.), as white solid melting at 248°–249° C.
Microanalysis:
Found: C 59,44; H 4,76; N 18,31;
Calculated for $C_{12}H_{11}N_3O_2$ : C 62,87; H 4,84; N 18,3
$^1$H-NMR (200 MH$_z$, Me$_2$SO-d$_6$) ppm:
4,50 (1H, dd, H$_{2a}$),
4,85 (1H, dd, H$_{2b}$),
5,24 (1H, t, H$_3$),
6,85–7,6 (6H, m, H$_6$+H$_7$+H$_8$+imidazole ring),
8,67 (1H,dd, H$_5$),
12,10 (1H, s,—=N—OH).
By the same procedure the following compound can be prepared: (+ −)-(E)-5-[2-(1H-imidazol-1-yl)-1,2,3,4-tetrahydro-1-naphtylidene]aminoxy] pentanoic acid (Comopound 32)
Microanalysis:
Found: C64,04; H 6,87; N 11,01;
Calculated for $C_{18}H_{21}N_3O_3$: C 66,04; H 6,46; N 12,83.
$^1$H-NMR (200 MH$_z$, CDCl$_3$) ppm:
1,75 (4H, m, —OCH$_2$CH$_2$CH$_2$—),
2,15–3,05 (4H, m, —CH$_2$COOH+H$_3$+H$_4$),
4,15 (2H, m, —OCH$_2$H$_2$—),
5,07 (1H, dd, H$_2$),
6,8–7,7 (6H, m, H$_5$+H$_6$+H$_7$+imidazole ring),
8,55 (1H, m, H$_8$).

EXAMPLE V (+ −)-(Z)-Ethyl-6-[[2-phenyl-3-(1H-imidazol-1-yl)-2,3-dihydro-4H-benzopyranylidene]aminoxy]hexanoate (Compound 6).

To a pentane-washed sodium hydride 55% (166 mg; 3.8 mmoles) suspension in dry DMF (10 ml), (+ −)-(Z)-2-phenyl-3-(1H-imidazol-1-yl)-2,3-dihydro-4H-benzopyran-4-one oxime (1 g.; 3.27 mmoles) suspended in dry DMF is added dropwise on stirring, under dry nitrogen atmosphere, at −78° C.

Then ethyl-6-bromohexanoate (1.16 ml; 6.5 mmoles) is added, and the resulting solution allowed to come up to room temperature.

The reaction mixture is poured into ice-water (3 g.), neutralized with acetic acid and extracted with ethyl acetate (3×20 ml).

The collected organic phases are washed with water (3×10 ml), dried over $Na_2SO_4$ and evaporated in vacuo. The resulting oily residue was chromatographed over silica gel column. By eluting with $CH_2Cl_2$/EtOH (98:2), the pure ester is obtained as light yellow oil, which crystallizes by treatment with hexane, to give 0.864 g. of white solid, melting at 65°–66° C.

Microanalysis:
Found: C 69,39; H 6,56; N 9,13;
Calculated for $C_{26}H_{29}N_3O_4$: C 69,78; H 6,53; N 9,39.
$^1$H-NMR: (200 MHz, $CDCl_3$) ppm:
1,22 (3H, t, —COO$CH_2$ $CH_3$),
1,1–1,7 (6H, m, —O$CH_2CH_2CH_2$$CH_2$),
2,23 (2H, t, —$CH_2$COO—),
4,0–4,2 (4H, m, —O$CH_2$CH$_2$—°—COO$CH_2$CH$_3$),
5,28 (1H, d, H$_2$),
5,68 (1H, d, H$_3$),
6,6–7,4 (11H, m, H$_6$+H$_7$+H$_8$+imidazole ring+phenyl ring),
8.0 (1H, m, H$_5$).

As an example the intermediate oxime used as starting material can be prepared as follows: (+ −)-2-phenyl-3-(1H-imidazol-1-yl)-2,3-dihydro-4H-benzopyran-4-one[J. Het. Chem. 21,311,(1984)], (4 g.; 0.014 moles), is dissolved in pyridine, and hydroxylamine hydrochloride (2.4 g.; 0.034 moles) dissolved in ethanol (20 ml), is added at room temperature to the solution.

The resulting solution is stirred overnight and the solvent is evaporated to provide a light yellow residue which crystallizes by treatment with water. The resulting solid material is recrystallized from ethanol to give 3.116 g. of pure oxime melting at 224°–225° C.

$^1$NMR: (80 MHz, $Me_2SO$-$d_6$)ppm:
5,58 (1H, d, H$_2$),
5,98 (1H, d, H$_3$),
6,6–7,6 (11H, m, H$_6$+H$_7$+H$_8$+imidazole ring+phenyl ring),
7,9 (1H, m, H$_5$).

By the same procedure the following compounds can be prepared:
(+ −)-Z-ethyl-5-[2-phenyl-3-(1H-imidazol-1-yl)-2,3-dihydro-4H-1-benzopyranylidene]aminoxy]pentanoate m.p. 86°–88° C. (Compound.8)
$^1$H-NMR(80 MHz, $CDCl_3$) ppm.
1,22 (3H, t, —COO$CH_2CH_3$)
1,45–1,7 (4H, m, —OCH$CH_2$CH$_2$)
2,25 (2H,m, —$CH_2$COO—)
4,0–4,2 (4H,m, —O$CH_2$CH$_2$—+—COO$CH_2$CH$_3$)
5,3 (1H,d, H$_2$)
5,73 (1H, d, H$_3$)
6,6–7,5 (11H, m, H$_6$+H$_7$+H$_8$+imidazole ring+phenyl ring)
8,0 (1H, m, H$_5$)

(+ −)-Z-Methyl-6-[[2-phenyl-3-(1H-imidazol-1-yl)-2,3-dihydro-6-methoxy-4H-1-benzopyranylidene]aminoxy]hexanote (Compound 12),
$^1$H-NMR (80 MH$_z$)($CDCl_3$):(Com.12) ppm:
1,1–1,9 (6H,m,—O$CH_2CH_2$,$_3$)
2,28 (2H,b, —$CH_2$COO)
3,68 (3H,s, —$CO_2CH_3$)
3,85 (3H,s, —O$CH_3$)
4,18 (2H,t, —O$CH_2$—)
5,23 (1H,d, H$_2$)
5,70 (1H,d, H$_3$)
6,60 (1H,bs, imidazole's H)
6,85 (1H,bs, imidazole's H)
7,0–7,50 (9H,m, H$_5$, H$_7$, H$_8$, imidazole's H phenyl ring)
And analogously:
3-[[2-(4-fluorophenyl)-3-(1H-imidazol-1-yl)-2,3-dihydro-6-fluoro-4H-1-benzopyranylidene]aminoxy]-propyloxy acetamide;(Compound 19)

EXAMPLE VI (+ −)-(Z)-6-[[2-phenyl-3-(1H-imidazol-1-yl)-2,3-dihydro-4H-benzopyranylidene]aminoxy]hexanoic acid (Compound 5)

(+ −)-(Z)-Ethyl-6-[[2-phenyl-3-(1H-imidazol-1-yl)-2,3-dihydro-4H-benzopyranylidene]aminoxy]hexanoate (300 mg; 0.67 mmoles) is dissolved in methanol-water (5:2; 7 ml), and to this solution sodium methylate (90 mg; 1.61 mmoles) is added portion-wise at 0° C. The resulting solution is stirred at r.t. for 28 hrs., then diluted with water, cooled at 0° C. and neutralized with acetic acid. The so formed precipitate is collected and recrystallized from ethyl acetate to give a white solid (190 mg), melting at 176°–178° C.

Microanalysis:
Found: C 68,54; H 6,06; N 9,91;
Calculated for $C_{24}H_{25}N_3O_4$: C 68, 72; H 6,01; N 10,02. $^1$H-NMR (200 MHz, $CDCl_3$) ppm:
0,9–1,7 (6H,m, O$CH_2CH_2CH_2CH_2$—)
2,15 (2H,m, —$CH_2$COOH)
4,15 (2H,m, —O$CH_2$CH$_2$CH$_2$—)
5,27 (1H,d,H$_2$)
5,69 (1H,d,H$_3$)
6,6–7,45 (11H,m,H$_6$+H$_7$+H$_8$30 imidazole ring+phenyl ring)
8.0 (1H,m,H$_5$)
By the same procedure the following compounds can be prepared:
(+ −)-(Z)-5-[[2-phenyl-3-(1H-imidazol-1-yl)-2,3-dihydro-4H-1-benzopyranylidene]aminoxy]pentanoic acid; (Compound 7).
mp: 163°–164° C.
Microanalysis: :
Found C 68,22; H 5,71; N 10,16
Calculated for $C_{23}H_{23}N_3O_4$ C 68,13; H5,71; N 10,36
$^1$H-NMR (200 MHz, $CDCl_3$) ppm:
1,4–1,7 (4H,m,—O$CH_2CH_2$CH$_2$—),
2,2 (2H,m,—$CH_2$COOH),
4,15 (2H,m,—O$CH_2$CH$_2$—),
5,28 (1H,d,H$_2$),
5,73 (1H,d,H$_3$),
6,6–7,4 (11H,m,H$_6$+H$_7$+H$_8$+imidazole ring+phenyl ring), 8.0 (1H,m,H$_5$).

4-[[2-(3,4-dimethoxyphenyl)-3-(1H-imidazol-1-yl)-2,3 dihydro-6-methoxy-4H-1-benzopyranylidene]aminoxy]butanoic acid;(Compound 9)

m.p. 220°–221° C.
Microanalysis:
Found: C 62,44; H 5,84; N 8,26;
Calculated for C$_{25}$H$_{27}$N$_3$O$_7$: C 62,36; H 5,65; N 8,73.
$^1$H-NMR (200 MHz,Me$_2$SO-d$_6$)ppm:
1,75 (2H,m, —OCH$_2$CH$_2$—)
2,13 (2H,m,—CH$_2$COOH)
3,55 (3H,s,—OCH$_3$)
3,69 (3H,s,—OCH$_3$)
3,76 (3H,s,—OCH$_3$)
4,12 (2H,m,—OCH$_2$CH$_2$—)
5,40 (1H,d,H$_2$)
5,80 (1H,d,H$_3$)
7,5–7,2 (8H, m, H$_7$+H$_8$+imidazole ring+phenyl ring)
7,33 (1H,d, H$_5$)

(+−)-(Z)-5-[[2-phenyl-3-(1H-imidazol-1-yl)-2,3-dihydro-6-methoxy-4H-1-benzopyranylidene]aminoxy]pentanoic acid; (Compound 10).

mp: 152°–155° C.
Microanalysis:
Found: C 65,22, H 5,71; N 9,49
Calculated for C$_{24}$N$_{25}$N$_3$O$_5$: C 66,19; H 5,78; N 9,65.
$^1$H-NMR (200 MHz,CDCl$_3$) ppm:
1,4–1,7 (4H,m,—OCH$_2$CH$_2$CH$_2$—),
2,15 (2H, m,—CH$_2$COOH),
3,83 (3H,s,—OCH$_3$),
4,17 (2H,m,—OCH$_2$CH$_2$—),
5,23 (1H,d,H$_2$),
5,68 (1H,d,H$_3$),
6,6–7,3 (10H,m,H$_7$+H$_8$+imidazole ring+phenyl ring),
7,42 (1H,d,H$_5$).

(+−)-(Z)-6-[[2-phenyl-3-(1H-imidazol-1-yl)-2,3-dihydro-6-methoxy-4H-1-benzopyranylidene]aminoxy]hexanoic acid; (Compound 11).

m.p. 159°–161° C.
Microanalysis:
Found: C 66,54; H 6,02; N 9,31
Calculated for C$_{25}$H$_{27}$N$_3$O$_5$: C 66,80; H 6,06; N 9,35
$^1$H-NMR (200 MHz, CDCl$_3$) ppm:
0,9–1,7 (6H, m, —OCH$_2$CH$_2$CH$_2$CH$_2$—)
2,15 (2H,m,—CH$_2$COOH)
3,83 (3H,s,—OCH$_3$)
4,15 (2H,m,—OCH$_2$CH$_2$—)
5,22 (1H,d,H$_2$).
5,65 (1H,d,H$_3$)
6,6–7,3 (10H,m,H$_7$+H$_8$+imidazole ring+phenyl ring)
7,42 (1H,d,H$_5$)

(+−)-(Z)-6-[[2-phenyl-3-(1H-imidazol-1-yl)-2,3-dihydro-6-nbutoxy-4H-1-benzopyranylidene]aminoxy]hexanoic acid; (Compound 13)

mp: 130°–134° C.
Microanalysis:
Found: C 67,66; H 6,76; N 8,36
Calculated for C$_{28}$H$_{33}$N$_3$O$_5$: C 68,41; H 6,77; N 8,55.
$^1$-NMR (200 MHz, CDCl$_3$) ppm:
0,97 (3H,t,—OCH$_2$CH$_2$CH$_2$CH$_3$)
0,95–1,85 (10H,m,—OCH$_2$CH$_2$CH$_2$CH$_3$ +—OCH$_2$CH$_2$CH$_2$CH$_2$—)
2,15 (2H,m,—CH$_2$COOH)
3,97 (2H,t,—OCH$_2$CH$_2$CH$_2$CH$_3$)
4,15 (2H,m,—OCH$_2$CH$_2$—)
5,21 (1H,d,H$_2$)
5,64 (1H,d,H$_3$)
6,6–7,3 (10H,m,H$_7$+H$_8$+imidazole ring+phenyl ring)
7,41 (1H,d,H$_5$).

(+−)-(Z)-5-[[2-(3,4-dimethoxyphenyl)-3-(1H-imidazol-1-yl)-2,3-dihydro-6-methoxy-4H-1-benzopyranylidene]aminoxy]pentanoic acid;(Compound 14)

mp: 201°–205° C.
Microanalysis:
Found: C 61,56; H 5,91; n 8,25
Calculated for C$_{26}$H$_{29}$N$_3$O$_7$: C 63,02; H 5,89; N 8,48.
$^1$h-NMR (200 MHz, Me$_2$SO-d$_6$)
1,35–1,65 (4H,m,—OCH$_2$CH$_2$CH$_2$—)
2,15 (2H,m,—CH$_2$COOH)
3,55 (3H,s,—OCH$_3$)
3,70 (3H,s,—OCH$_3$)
3,76 (3H,s,—OCH$_3$)
4,10 (2H,m,—OCH$_2$CH$_2$)
5,41 (1H,d,H$_2$)
5,78 (1H,d,H$_3$)
6,5–7,2 (8H,m,H$_7$+H$_8$+imidazole ring+phenyl ring)
7,33 (1H,d,H$_5$).

(+−)-(Z)-6-[[2-(3,4-dimethoxyphenyl)-3-(1H-imidazol-1-yl)-2,3-dihydro-6-methoxy-4H-1-benzopyranylidene]aminoxy]hexanoic acid;(Compound 15)

mp: 203°–206° C.
Microanalysis: :
Found: C 62,75; H 6,28; N 8,02;
Calculated for C$_{27}$H$_{31}$N$_2$O$_7$: C 63,64; H 6,13; N 8,25.
$^1$H-NMR (200 MHz, me$_2$SO-d$_6$)ppm:
1.0–1,6 (6H,m,—OCH$_2$CH$_2$CH$_2$CH$_2$—)
1,8 (2H,m,—CH$_2$COOH)
3,55 (3H,s,—OCH$_3$)
3,69 (3H,s,—OCH$_3$)
3,76 (3H,s,—OCH$_3$)
4,08 (2H,m,—OCH$_2$CH$_2$—)
5,41 (1H,d,H$_2$)
5,78 (1H,d,H$_3$)
6,5–7,15 (8H,m,H$_7$+H$_8$+imidazole ring+phenyl ring)
7,33 (1H,d,H$_5$)

(+−)-(Z)-6-[[2-phenyl-3-(1H-imidazol-1-yl)-2,3-dihydro-6-fluoro-4H-1-benzopyranylidene]aminoxy]hexanoic acid; (Compound 17).

mp: 179°–181° C.
Microanalysis:
Found: C 65,47; H 5,56; n 9,59;
Calculated for C$_{24}$H$_{25}$N$_3$FO$_4$: C 65,89; H 5,53; N 9,60.
$^H$-NMR (200 MHz,CDCl$_3$)ppm:
0,9–1,7 (6H, m, —OCH$_2$ CH$_2$ CH$_2$ H$_2$—)
2,15 (2H,m, —CH$_2$COOH)
4,15 (2H, m, —OCH$_2$CH$_2$—)
5,24 (1H, d, H$_2$)
5,65 (1H, d, H$_3$)
6,6–7,35 (10H, m, H$_7$+H$_8$+imidazole ring+phenyl ring)
7.65 (1H, m, H$_5$).

(+−)-(Z)-6-[[2-benzyl-3-(1H-imidazol-1-yl)-2,3-dihydro-4H-1-benzopyranylidene]amnoxy]hexanoic acid;(Compound 29)

mp: 74°–76° C.
Microanalysis:
Found: C 68,76; H 6,28; N 9,50;
Calculated for C$_{25}$H$_{27}$N$_3$O$_4$ C 69,26; H 6,28; N 9,69.

¹H-NMR (200 MHz, CDCl₃)ppm:
1,0-1,75 (6H, m, —OCH₂CH₂CH₂CH₂—)
2,25 (2H, m, —CH₂COOH)
2,63 (1H, d.d, —CHH-Ph)
2,95 (1H, d.d, —CHH-Ph)
4,1 (2H, m, —OCH₂CH₂—)
4,41 (1H, d.t, H₂)
5,47 (1H, d, H₃)
6,85-7,7 (11H, m, H₆+H₇+H₈+imidazole ring+phenyl ring)
7,88 (1H, m, H₅).

(+ −)-(Z)-5-[[2-(thien-2-yl)-3-(1H-imidazol-1-yl)-2,3-dihydro 4H-1-benzopyranylidene]aminoxy]pentanoic acid. (Compound 24):
mp. 138°-139° C.
Microanalysis: found C 60.60; H 5.54; N 9.54; Calculated for C₂₁H₂₁N₃O₄S: C 61.30; H 5.15; N 10.21.
¹H-NMR: (200 MHz; CDCl₃) ppm:
1,4-1,8 (4H, m, CH₂-(CH₂)₂—CH₂),
2,25 (2H, 7, CH₂COO),
4,15 (2H, t, OCH₂),
5,55 (1H, d, H₂),
5,78 (1H, d, H₃),
6,75-7,50(9H, m, Aromatic H's),
7,96 (1H, d, H₅).

(+ −)-(Z)-5-[[2-(thien-3-yl)-3-(1H-imidazol-1-yl)-2,3-dihydro -F4H-1-benzopyranylidene]aminoxy]pentanoic acid (Compound 26).
mp. 150°-151° C.
Microanalysis: found C 61,61; H 5,34; N 9.96; Calculated for C₂₂H₂₁N₃O₄S: C 61,30; H 5,15; N 10,21. ¹H-NMR: (80 MHz; CDCl₃) ppm: 1,4-1,8 (4H, m, CH₂—(CH₂)₂—CH₂) 2,1-2,4 (2H, t, CH₂ COOO) 4,1-4.3 (2H, t, CH₂ O) 5,38 (1H, d, H₂) 5,75 (1H, d, H₃) 6,7-7,5 (9H, m, Aromatic H's) 8,01 1H, dd, H₅).

(+ −)-(Z)-6-[[2-(thien-3-yl)-3-(1H-imidazol-1-yl)-2,3-dihydro -4H-1-benzopyranylidene]aminoxy]hexanoic acid; (Compound 27).
mp. 149°-150° C.
Microanalysis: found: C 62.09; H 5.45; N 9.88; calculated for C₂₂H₂₃N₃O₄S: C 62.45; H 5.53; N 9.81;
¹H-NMR (80 MHz; CDCl₃) ppm: 1,0-1,8 (6H, m, (CH₂)₃) 2.21 (2H, t, CH₂ COO) 4,18 (2H, t, CH₂ O) 5,40 (1H, d, H₂) 5,72 (1H, d, H₃) 6,74-7,50 (9H, m, Aromatic H's) 8.02 (1H, dd, H₅)

And analogously:
5-[[2-(4-fluorophenyl)-3-(1H-imidazol-1-yl)-2,3-dihydro-6-fluoro-4H-1-benzopyranylidene]aminoxy]pentanoic acid; (Compound 16)
3-[[2-(4-fluorophenyl)-3-(1H-imidazol-1-yl)-2,3-dihy dro-6-fluoro-4H-1-benzopyranylidene]aminoxy]-propyloxyacetic acid; (Compound 18)
5-[[2-(4-fluorophenyl)-3-(1H-imidazol-1-yl)-2,3-dihydro-6-fluoro-4H-1-benzopyranylidene]aminoxy]pentyloxyacetic acid; (Compound 20)
2-[[2-(4-fluorophenyl)-3-(1H-imidazol-1-yl)-2,3-dihydro-6-fluoro-4H-1-benzopyranylidene]aminoxy]ethyloxyacetic acid; (Compound 21)
6-[[2-(thien-2-yl)-3-(1H-imidazol-1-yl)-2,3-dihydro -4H-1-benzopyranylidene]aminoxy]hexanoic acid; (Compound 25)
3-[[2-(4-fluorophenyl)-3-(1H-imidazol-1-yl)-2,3-dihydro -6-trifluoromethyl-4H-1-benzopyranylidene]aminoxy]propyloxyacetic acid; (Compound 28)
2-[[2-((4-fluorophenyl)methyl)-3-(1H-imidazol-1-yl)-2,3-dihydro-6-fluoro-4H-1-benzopyranylidene]aminoxy]ethyloxyacetic acid; (Compound 30)
6-[[2-phenyl-3-((1H-imidazol-1-yl)methyl)-2,3-dihydro -4H-1-benzopyranylidene]aminoxy]hexanoic acid; (Compound 31)
5-[[2-phenyl-3-(1-H-imidazol-1-yl)-2,3-dihydro 4H-1-benzopyranylidene]aminoxy]-2-pentenoic acid;
6-[[2-phenyl-3-(1-H-imidazol-1-yl)-2,3-dihydro 4H-1-benzopyranylidene]aminoxy]-2-hexenoic acid, and
5-[[2-phenyl-3-(1-H-imidazol-1-yl)-2,3-dihydro 4H-1-benzopyranylidene]aminoxy]-3,3-dimethyl pentanoic acid.

EXAMPLE VII (+ −)-(Z)-5-[[2-phenyl-3-(1H-imidazol-1-yl)-2,3-dihydro-4H-benzopyranylidene]aminoxy]pentanoic acid (Compound 7).

(+ −)-2-phenyl-3-(1H-imidazol-1-yl)-2,3-dihydro-4H-benzopyran-4-one (580 mg.; 2 mmoles), is dissolved in dry pyridine (30ml), to this solution 5-aminooxypentanoic acid hydrochloride (510 mg.; 3 mmoles), is added portionwise at 0° C. The resulting solution is then allowed to come up to room temperature and stirred overnight. The solvent is then evaporated in vacuo and the oily residue is taken up with water, glacial acetic acid is added until pH 5, and the aqueous phase is extracted with ethyl acetate (3×40 ml), the resulting organic layer is washed with water, dried over Na₂SO₄, and evaporated in vacuo. Silica gel column chromatography affords by eluting with CH₂Cl₂MeOH (95:5), the pure titled compound (700 mg.; 86%), as colorless solid melting at 166°-67° C. (etyl ether/hexane).
Microanalysis: Found C 68,18; H 5.65; N 10.28; Calculated for C₂₃H₂₃N₃O₄: C 68.134; H 5.71; N 10.36.

As an example the intermediate 5-aminooxypentanoic acid used as starting material can be prepared as follows:

N-hydroxyphthalimide sodium salt (6.6 g.; 36 mmoles), is dissolved in dry DMF (120 ml), to the resulting dark red solution Ethyl 5-bromopentanoate (7.3 ml.; 43 mmoles) is added at room temperature, on stirring. The reaction mixture is stirred at 50° C. for six hours, under dry nitrogen atmosphere, and then poured into 500 g. of crushed ice. The resulting aqueous phase is extracted with ethyl acetate (4×100 ml.), the collected organic layers are washed with water, dried over Na₂SO₄, and evaporated in vacuo to provide an oily material which crystallize by treatment with hexane, to provide ethyl N-5-phthalimidoaminooxypentanoate (9.2 g.; 86%), m.p. 57°-58° C.

¹H-NMR (80 MHz, CDCl₃) ppm:
1.25 (3H, t, CH₃),
1.88 (2H, m, CH₂CH₂),
2.45 (2H, m, CH₂OOO),
4.10 (2H, t, CH₂CH₃),
4.32 (2H, m, N—O—CH₂),
7.80 (4H, m, phenyl ring).

The above described ethyl N-5-phthalimidooxypentanoate (9 g., 30 mmoles), is dissolved in 95% ethanol (100 ml.), to this solution NaOH 2N (25 ml.), is added dropwise at 0° C. The resulting solution is stirred at room temperature 2 hrs., the solution is concentrated to half a volume, and NaOH 15(50 ml) is added. The resulting reaction mixture is stirred at room temperature overnight, ethanol is evaporated in vacuo ten on cooling at 0° C., 37% HCl is added until pH 1, the so obtained aqueous solution is washed with ethyl acetate to remove phthalic acid, and evaporated to dryness in vacuo. The resulting residue is taken up with cold ethanol, the insoluble is filtered, and the filtrate is concentrate in vacuo. The pure 5-aminooxypentanoic acid hydrochloride (4.6 g.) precipitate on standing, m.p. 127°–129° C.

And analogously the following compounds can be obtained:

6-[[2-phenyl-3-(1H-imidazol-1-yl)-2,3-dihydro-4H-1-benzopyranylidene]aminoxy]hexanoic acid (Compound 5);

5-[[2-phenyl-3-(1-H-imidazol-1-yl)-2,3-dihydro-4H-1-benzopyranylidene] aminoxy]-2-pentenoic acid (Compound 38); and 6-[[2-phenyl-3-(1-H-imidazol-1-yl)-2,3-dihydro-4H-1-benzopyranylidene]-2-hexanoic acid (Compound 39).

EXAMPLE VIII

| | |
|---|---|
| (Z)-5-[[2,3-dihydro-3-(1H-imidazol-1-yl)-4H-1-benzopyranylidene] aminoxyl] pentanoic acid | 500 g |
| Lactose | 710 g |
| Corn starch | 237.5 g |
| Talc powder | 37.5 g |
| Magnesium stearate | .15 g |

(Z)-5-[[2,3-dihydro-3-(1H-imidazol-1-yl)-4H-1-benzopyranylidene]aminoxy] pentanoic acid, lactose and a half of the corn starch are mixed: the mixture is then forced through a sieve of 0.5 mm openings. Corn starch (18 mg) is suspended in warm water (180 ml). The resulting paste is used to granulate the powder. The granules are dried, comminuted on a sieve of sieve size 1.4 mm, then the remaining quantity of starch, talc and magnesium are added, carefully mixed, and processed into tablets using punches of 8 mm diameter.

We claim:

1. A compound of formula (I)

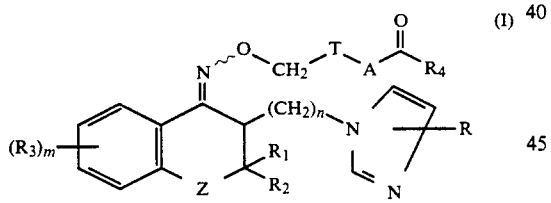

wherein
Z is —CH$_2$— or —O—;
m is an integer of 1 to 4;
n is zero or 1;
T is a straight or branched C$_1$–C$_6$ alkylene chain or C$_2$–C$_5$ alkenylene chain;
A is a bond or a divalent group consisting of —Si(R'R")—; —O—CH$_2$—, —CF$_2$—, C(R'R")—, vinylene or isopropenylene, wherein each of R' and R" being the same or different is hydrogen or C$_1$–C$_4$ alkyl;
R is hydrogen or C$_1$–C$_4$ alkyl;
R$_1$ and R$_2$, being the same, are hydrogen or methyl, or one of R$_1$ and R$_2$ is hydrogen and the other is:
a) a C$_1$–C$_8$ alkyl group;
b) a C$_5$–C$_8$ cycloalkyl or C$_5$–C$_8$ cycloalkyl-C$_1$–C$_4$ alkyl group, wherein the cycloalkyl group or moiety is unsubstituted or substituted by 1 to 4 C$_1$–C$_4$ alkyl groups; or c) a member selected from the group consisting of phenyl, pyridyl, naphthyl, thienyl, phenyl-C$_1$–C$_2$ alkyl group, pyridyl-C$_1$–C$_2$ alkyl group, naphthyl-C$_1$–C$_2$ alkyl group and thienyl-C$_1$–C$_2$ alkyl group which is unsubstituted or substituted by 1 to 4 substituents independently chosen from halogen, hydroxy, C$_1$–C$_4$ alkyl, trihalo-C$_1$–C$_4$ alkyl, C$_1$–C$_4$ alkoxy, C$_1$–C$_4$ alkylthio and C$_1$–C$_4$ alkylsulfonyl;
R$_3$ is hydrogen or a substituent chosen from halogen, hydroxy, C$_1$–C$_4$ alkyl, trihalo-C$_1$–C$_4$ alkyl, C$_1$–C$_4$ alkoxy, C$_1$–C$_4$ alkylthio and C$_1$–C$_4$ alkylsulfonyl;
R$_4$ is an —OR$_5$ or N(R$_5$ R$_6$) group, wherein each of R$_5$ and R$_6$ independently is hydrogen, C$_1$–C$_6$ alkyl, phenyl or benzyl, or the pharmaceutically acceptable salt thereof.

2. A compound of formula (I), according to claim 1, wherein
Z is —CH$_2$— or —O—;
m is 1 or 2;
n is zero;
T is a C$_2$–C$_5$ alkylene or C$_2$–C$_5$ alkenylene chain;
A is a bond or a divalent group chosen from —O—CH$_2$—, —CF$_2$—, —C(R'R")— and Si(R'R'')—, wherein each of R' and R", being the same or different is hydrogen or methyl;
R is hydrogen;
R$_1$ and R$_2$ are both hydrogen, or one of R$_2$ and R$_2$ is hydrogen and the other is:
a') C$_1$–C$_4$ alkyl;
b') a C$_5$–C$_7$ cycloalkyl or C$_5$–C$_7$ cycloalkyl-methyl group;
c') a phenyl or benzyl group, wherein the phenyl ring or the phenyl moiety is unsubstituted or substituted by one, two or three substituents independently chosen from halogen, hydroxy, C$_1$–C$_4$ alkyl, trihalo-C$_1$–C$_4$ alkyl, C$_1$–C$_4$ alkoxy, alkylthio and C$_1$–C$_4$ alkylsulfonyl; or
d) a thienyl, thienylmethyl, pyridyl or pyridylmethyl group, wherein the heterocyclic ring or moiety is unsubstituted or substituted by one or two substituents chosen from halogen, trifluoromethyl, hydroxy, C$_1$–C$_4$ alkyl and C$_1$–C$_4$ alkoxy;
R$_3$ is hydrogen, halogen, trifluoromethyl, C$_1$–C$_4$ alkylsulfonyl or C$_1$–C$_4$ alkoxy;
R$_4$ is an —OR$_5$ or —NHR$_5$ group, wherein R$_5$ is hydrogen or C$_1$–C$_4$ alkyl; or the pharmaceutically acceptable salt thereof.

3. A compound selected from the following compounds, either as Z or E isomers or Z,E-mixtures of said isomers:

5-[[2,3-dihydro-3-(1H-imidazol-1-yl)-4H-1-benzopyranylidene]aminoxy]pentanoic acid;

5-[[2-methyl-3-(1H-imidazol-1-yl)-2,3-dihydro-4H-1-benzopyranylidene]aminoxy]pentanoic acid;

Ethyl-5-[[2-methyl-3-(1H-imidazol-1-yl)-2,3-dihydro-4H-1-benzopyranylidene]aminoxy]pentanoate;

6-[[2-methyl-3-(1H-imidazol-1-yl)-2,3-dihydro-4H-1-benzopyranylidene]-aminoxy]hexanoic acid;

6-[[2-phenyl-3-(1H-imidazol-1-yl)-2,3-dihydro-4H-1-benzopyranylidene]aminoxy]hexanoic acid;

Ethyl-6-[[2-phenyl-3-(1H-imidazol-1-yl)-2,3-dihydro-4H-1-benzopyranylidene]aminoxy]hexanoate;

5-[[2-phenyl-3-(1H-imidazol-1-yl)-2,3-dihydro-4H-1-benzopyranylidene]aminoxy]pentanoic acid;

Ethyl-5-[[2-phenyl-3-(1H-imidazol-1-yl)-2,3-dihydro-4H-1-benzopyranylidene]aminoxy]pentanoate;

4-[[2-(3,4-dimethoxyphenyl)-3-(1H-imidazol-1-yl)-2,3-dihydro-6-methoxy-4H-1-benzopyranylidene]aminoxy]butanoic acid;

5-[[2-phenyl-3-(1H-imidazol-1-yl)-2,3-dihydro-6-methoxy-4H-1-benzopyranylidene]aminoxy]pentanoic acid;

6-[[2-phenyl-3-(1H-imidazol-1-yl)-2,3-dihydro-6-methoxy-4H-1-benzopyranylidene]aminoxy]hexanoic acid;

Methyl-6-[[2-phenyl-3-(1H-imidazol-1-yl)-2,3-dihydro-6-methoxy-4H-1-benzopyranylidene]aminoxy]hexanoate; independently chosen from halogen, hydroxy, [$C_{1-p}$ 6-[[2-phenyl-3-(1H-imidazol-1-yl)-2,3-dihydro-6-nbutoxy-4H-1-benzopyranylidene]aminoxy]hexanoic acid;

5-[[2-(3,4-dimethoxyphenyl)-3-(1H-imidazol-1-yl)-2,3-dihydro-6-methoxy-4H-1-benzopyranylidene]aminoxy]pentanoic acid;

6-[[2-(3,4-dimethoxyphenyl)-3-(1H-imidazol-1-yl)-2,3-dihydro-6-methoxy-4H-1-benzopyranylidene]aminoxy]hexanoic acid;

5-[[2-(4-fluorophenyl)-3-(1H-imidazol-1-yl)-2,3-dihydro-6-fluoro-4H-1-benzopyranylidene]aminoxy]pentanoic acid;

6-[[2-phenyl-3-(1H-imidazol-1-yl)-2,3-dihydro-6-fluoro-4H-1-benzopyranylidene]aminoxy]hexanoic acid;

3-[[2-(4-fluorophenyl)-3-(1H-imidazol-1-yl)-2,3-dihydro-6-fluoro-4H-1-benzopyranylidene]aminoxy]propyloxyacetic acid;

3-[[2-(4-fluorophenyl)-3-(1H-imidazol-1-yl)-2,3-dihydro-6-fluoro-4H-1-benzopyranylidene]aminoxy]propyloxyacetamide;

5-[[2-(4-fluorophenyl)-3-(1H-imidazol-1-yl)-2,3-dihydro-6-fluoro-4H-1-benzopyranylidene]aminoxy]pentyloxyacetic acid;

2-[[2-(4-fluorophenyl)-3-(1H-imidazol-1-yl)-2,3-dihydro-6-fluoro-4H-1-benzopyranylidene]aminoxy]ethyloxyacetic acid;

6-[[2-cyclohexyl-3-(1H-imidazol-1-yl)-2,3-dihydro-6-fluoro-4H-1-benzopyranylidene]aminoxy]hexanoic acid; 2-[[2-cyclohexyl3-(1H-imidazol-1-yl)-2,3-dihydro-6-fluoro-4H-1-benzopyranylidene]aminoxy]propyloxyacetic acid;

5-[[2-(thien-2-yl)-3-(1H-imidazol-1-yl)-2,3-dihydro-4H-1-benzopyranylidene]aminoxy]pentanoic acid;

6-[[2-(thien-2-yl)-2,3dihydro-4H-1-benzopyranylidene]aminoxy]hexanoic acid;

5-[[2-(thien-3-yl)-3-(1H-imidazol-1-yl)-2,3-dihydro-4H-1-benzopyranylidene]aminoxy]pentanoic acid;

6-[[2-(thien-3-yl)-3-(1H-imidazol-1-yl)-2,3-dihydro-4H-1-benzopyranylidene]aminoxy]hexanoic acid;

3-[[2-(4-fluorophenyl)-3-(1H-imidazol-1-yl)-2,3-dihydro-6-trifluoromethyl-4H-1-benzopyranylidene]aminoxy]propyloxyacetic acid;

6-[[2-benzyl-3-(1H-imidazol-1-yl)-2,3-dihydro-4H-1-benzopyranylidene]aminoxy]hexanoic acid;

2-[[2-((4-fluorophenyl)methyl)-3-(1H-imidazol-1-yl)-2,3-dihydro-6-fluoro-4H-1-benzopyranylidene]aminoxy]ethyloxyacetic acid;

6-[[2-phenyl-3-((1H-imidazol-1-yl)methyl)-2,3-dihydro-4H-1-benzopyranylidene]aminoxy]hexanoic acid;

5-[[2-(1H-imidazol-1-yl)-1,2,3,4-tetrahydro-1-naphthylidene]aminoxy]pentanoic acid;

5-[[2-(1H-imidazol-1-yl)-7-methoxy-1,2,3,4-tetrahydro-1-naphthylidene]aminoxy]pentanoic acid;

Ethyl-5-[[2-(1H-imidazol-1-yl)-1,2,3,4-tetrahydro-1-naphthylidene]aminoxy]pentanoate;

5-[[2-(1H-imidazol-1-yl)-3-methyl-1,2,3,4-tetrahydro-1-naphthylidene]aminoxy]pentanoic acid;

6-[[2-1H-imidazol-1-yl)-3-methyl-1,2,3,4-tetrahydro-1-naphthylidene]aminoxy]hexanoic acid;

6-[[2-(1H-imidazol-1-yl)-3-phenyl-1,2,3,4-tetrahydro-1-naphthylidene]aminoxy]hexanoic acid;

5-[[2-phenyl-3-(1-H-imidazol-1-yl)-2,3-dihydro 4H-1-benzopyranylidene]aminoxy]-2-pentenoic acid;

6-[[2-phenyl-3-(1-H-imidazol-1-yl)-2,3-dihydro 4H-1-benzopyranylidene]aminoxy]-2-hexenoic acid;

5-[[2-phenyl-3-(1-H-imidazol-1-yl)-2,3-dihydro 4H-1-benzopyranylidene]aminoxy]-3,3-dimethyl pentanoic acid, or the pharmaceutically acceptable salt thereof.

4. A pharmaceutical composition comprising a suitable carrier and/or diluent and, as an active principle, an effective amount of a compound of formula (I) or a pharmaceutically acceptable salt thereof as claimed in claim 1.

5. A method for treatment of a disease state in which enhancement of $TXA_2$ synthesis exerts a pathogenic effect comprising: administering an effective amount of the compound of claim 1 to an individual in need thereof.

6. A method for treating cardiovascular disease, cerebrovascular disease, peripheral vascular disease, renal disease, respiratory disease or atherosclerosis comprising: administering an effective amount of the compound of claim 1 to an individual in need thereof.

* * * * *